United States Patent [19]  [11] 4,366,088
Daniel  [45] Dec. 28, 1982

[54] SUPPORT FOR A PHOSPHATE-CONTAINING CATALYST

[75] Inventor: Chelliah Daniel, Columbus, Ohio

[73] Assignee: Ashland Oil, Inc., Ashland, Ky.

[21] Appl. No.: 228,304

[22] Filed: Jan. 26, 1981

[51] Int. Cl.³ .......................................... B01J 27/14
[52] U.S. Cl. ................................. 252/435; 252/437
[58] Field of Search ............................. 252/437, 435

[56] References Cited

U.S. PATENT DOCUMENTS

| | | | |
|---|---|---|---|
| 2,057,433 | 10/1936 | Ipatieff | 252/435 X |
| 2,220,430 | 11/1940 | Stanley | 252/435 X |
| 3,327,009 | 6/1967 | Noddings et el. | 252/437 X |
| 3,449,436 | 6/1969 | O'Connor et al. | 252/435 X |
| 3,459,678 | 8/1969 | Hagemeyer et al. | 252/435 |
| 3,660,514 | 5/1972 | Cichowski et al. | 260/680 E |
| 3,679,601 | 7/1972 | Nolan et al. | 252/437 |
| 3,697,550 | 10/1972 | Boyne et al. | 252/435 X |
| 3,716,545 | 2/1973 | Ripley | 252/437 X |
| 3,855,279 | 10/1974 | Watkins | 252/437 X |
| 3,927,138 | 12/1975 | Walker | 585/623 |
| 3,993,591 | 11/1976 | Cichowski et al. | 252/437 X |
| 4,010,114 | 3/1977 | Walker et al. | 252/435 X |
| 4,202,798 | 5/1980 | Johnson et al. | 252/437 |

*Primary Examiner*—Delbert E. Gantz
*Assistant Examiner*—William G. Wright
*Attorney, Agent, or Firm*—Wood, Herron & Evans

[57] ABSTRACT

A support for a phosphate-containing catalyst comprising a combination of an inert material such as silica and phosphoric acid. The support is formed by mixing the inert support and the phosphoric acid together to form a slurry, evaporating the liquid off and calcining the resulting mass. This support is used in combination with phosphate-containing catalysts to overcome the deactivation of these catalysts caused by the leaching of phosphate ions from the catalyst. This catalyst support has found particular utility in combination with an iron/phosphorus oxidation catalyst and even more particularly, in use with an iron phosphorous catalyst used in the oxydehydrogenation of isobutyric acid to form methacrylic acid.

7 Claims, No Drawings

SUPPORT FOR A PHOSPHATE-CONTAINING CATALYST

BACKGROUND OF THE INVENTION

This invention relates to a catalyst support for use in combination with a phosphate-containing catalyst. More particularly, this invention relates to a catalyst support for use with a phosphate-containing catalyst in a reaction where phosphorus in the form of a phosphate is being withdrawn or leached from the catalyst, thereby reducing the catalyst's effectiveness.

Phosphates are frequently employed as catalysts in various reactions, particularly in combination with iron or calcium, and possibly alkali or alkaline earth metals for use as mild oxidative catalysts. However, over a long period of continued use, these catalysts tend to deactivate because the phosphorus is slowly leached from the catalyst. This is particularly a problem in a continuous reaction where reactants flow over or through a catalyst bed. Several solutions have been suggested for this problem, particularly, the addition of phosphates into the feed or increasing the molar proportion of phosphates in the catalyst. These solutions have proved to be somewhat ineffective in preventing the deactivation of the catalyst.

It has been found that by using a phosphate-doped catalyst support which is physically mixed with the phosphate catalyst, the problem of phosphate leaching is substantially reduced or eliminated. The particular catalyst supports employed in the present invention comprises a mixture of an inert material, such as silica, titania, or zirconia in combination with a phosphate, preferably phosphoric acid.

DETAILED DESCRIPTION OF THE INVENTION

The present invention comprises a support for a phosphate containing catalyst which compensates the loss of phosphorus during the use of the catalyst.

Phosphates in combination with other metals such as iron, nickel, copper, lead and calcium are frequently used as mild oxidizing catalysts. One major problem encountered when using such a catalyst is the leaching of phosphates from the catalyst during use. Over a prolonged period of time this leaching of phosphorus from the catalyst decreases the effectiveness of the catalyst.

The present invention overcomes this problem by combining the phosphate catalysts with a phosphate doped support. The catalyst and phosphate doped support should be mixed when both the support and the catalyst are in a substantially dry state. In other words, if the individual components of the phosphate-doped support are added to the catalyst during the formation of the catalyst, the phosphate leaching will not be stopped.

A support for a catalyst is generally a material which is inert and used for the purpose of adding strength or increased surface area to the catalyst. Such supports are generally used with heterogeneous catalysts. Some typical supports include silica, titania and zirconia.

The phosphate doped support of the present invention is formed by forming a liquid slurry and preferably an aqueous slurry comprising a phosphate containing compound and an inert support material. This slurry is then dried at about 120° C. and calcined at about 450° C. for approximately 15 hours.

For use in the present invention any phosphate containing compound may be used. Included within the term phosphate are the pyrophosphates. The preferred source of phosphates are the inorganic phosphorus acids and most preferred is phosphoric acid.

For the purposes of the present invention, any support material which remains inert during the preperation of the phosphate doped support and inert during the use of the catalyst will function properly in the present invention. Preferred supports are silica, zirconia, titania, silica being the most preferred.

The molar ratio of phosphate to inert support material can vary substantially. Generally a ratio of phosphate to support can vary from 20:1 to 1:3. At this point, no preferred ratio has been determined. The ratio will, of course, vary according to the type of support material used with consideration being given to the proper functioning of the support with respect to imparting strength and surface area to the catalyst.

Once the phosphate doped support has been prepared, it is physically mixed with the phosphate catalyst. This mixing should occur when both the phosphate dope support and the phosphate catalyst have been prepared and are dry.

For purposes of describing this invention as well as describing the preferred embodiment of this invention, this catalyst is described for use with an iron phosphate catalyst. In addition, the use of this catalyst and support combination is described for use catalyzing the oxydehydrogenation of isobuteric acid to form methacrylic acid. Again, this is by way of example as well as a description of the most preferred embodiment of this invention.

Iron phosphate-type catalysts are disclosed in Cavaterra U.S. Pat. No. 3,948,959, and are well known to those skilled in the art. Cavaterra teaches the preparation of a catalyst having a mixture of iron phosphorus oxygen, and optionally, lithium, sodium, potassium, rubidium, cesium, magnesium, calcium, stontium, or barium. Proportions of these elements contained in the catalyst of the present invention can be expressed by the following formula: Fe $P_xMe_yO_z$ wherein Me is one or more of the following elements: lithium, sodium, potassium, rubidium, cesium, magnesium, calcium, strontium or barium; x is 0.2 to 2.0 and preferably, 0.8 to 1.4; y is 0.10 to 2.0, and z has a value sufficient to compensate the average valences of the elements in the oxidation states in which they exist in the catalyst. It is conventional in this art to identify the catalyst by empirical formula and to consider the elements existing as oxides. However, it is understood by those skilled in the art to assign a value to a symbol such as z in the foregoing formula is not to say that all the elements making up the catalyst do exist as oxides, particularly since the actual oxidation state of the elements as they exist in the catalyst has not been established.

For this invention, the following salts are suitable sources of iron: nitrates, halides, sulfates, carbonates, salts of monocarboxylic and polycarboxylic organic acids and oxides.

Sources of phosphorus include alkaline phosphates, ammonium phosphates and phosphoric acid, phosphoric acid being the preferred source of phosphorus.

The following sources of alkali or alkaline earth metals, for example, may be used: nitrates, oxides, hydroxides, carbonates, bicarbonates, nitriles, phosphates, silicates and oxyacid salts of monocarboxylic or polycarboxylic acids such as formates, oxylates, citrates, tartrates, etc.

The catalyst is prepared by first dissolving a desired quantity of the iron-containing compound in a solvent, preferably water. A suitable quantity of phosphorus in the form of an acid or dissolved salt solution is admixed with the iron solution. Silica can also be added up to about 15% to give the catalysts a desired physical strength. This should not be confused with the silica used in the formation of the support.

The pH of this solution is adjusted to 7 by the addition of a base, preferably ammonium hydroxide, causing a yellow precipitate to form. The precipitate is a raw iron/phosphate catalyst. This precipitate is washed by decanting with water until the decanting water contains no dissolved solids. The washed catalyst is dried by gently heating at a temperature of approximately 50° C. If the alkali or alkaline earth metals are desired in the catalyst, the salts of these metals are dissolved in the slurried precipitate during the above heating. This final mixture is heated at 100° C. to dryness.

An alternate method of preparing this catalyst is disclosed in Cavaterra which calls for the addition of the alkali or alkaline earth metal to the iron phosphorus solution prior to neutralization. The remaining steps are not altered. It is believed that adding of the alkaline metals prior to heating causes the catalysts to be more homogenous. This dry catalyst is crushed to desired fineness and calcined.

Other phosphate-containing catalysts are disclosed in the final patents:

| Inventor | Pat. No. | Elements of Catalyst |
| --- | --- | --- |
| Walker et al | 4,010,114 | Fe/Sn/P/alkaline Metal/O |
| Walker | 3,927,138 | (Ni,Cu,Fe)/Sn/P/alkali earth metal/O |
| Watkins | 3,855,279 | Fe/Pb/P/O |
| Cichowski | 3,993,591 | Fe/P/Group IIIA/O |
| Noddings et al | 3,327,009 | Ca/Fe/P/O |
| Ripply | 3,716,545 | Fe/P/O |

As shown below, a catalyst containing a phosphate moiety when used over a prolonged period of time tends to be deactivated. This is partially due to phosphate leaching from the catalyst.

Several solutions have been proposed to this problem such as adding a greater than stoichiometric amount of phosphates to the catalyst or continuously or intermittently adding phosphoric acid or some other phosphate-containing compound into the reaction vessel. Although these succeed to some degree, as shown by the examples presented below, the phosphate leaching problem can best be solved by mixing the phosphate-doped support of the present invention with the catalyst. In addition, as example V indicates, the present invention is superior to a catalyst in which the support is mixed with the catalyst during the preparation of the catalyst.

According to this invention, the dry phosphate-doped support prepared as described above is physically mixed with the dry phosphate catalyst. The percentage of catalyst support in the catalyst support mixture or system can vary from 50 to 80%. Both the phosphate catalyst and the support should be in a substantially dry state at this point.

This support-catalyst mixture or system is useful in the dehydrogenation of alkanes and olefins. In order to show the utility of these catalysts as well as disclosing a preferred embodiment of this invention, the following description of the oxidative dehydrogenation of isobutyric acid to form methacrylic acid is disclosed. In this reaction, the isobutyric acid in a gaseous mixture with oxygen from air and one or more diluents such as nitrogen, steam or carbon dioxide is passed through the reaction chamber wherein the mixture of the iron/phosphate catalyst and catalyst support is contained. Preferably, the reactor is a tubular reactor, but other reaction vessels can be used as well.

The amount of saturated acid contained in a reaction mixture is generally 1 to 35% by volume and preferably, 5.0 to 10% by volume. The reaction is preferably conducted using a fixed catalytic bed and is conducted at a temperature from about 300° C. to 500° C. and, preferably, from 340° C. to 400° C.

The contact time expressed in seconds is the ratio between the volume of the catalyst bed and the volume of the gaseous mixture reagents fed per second at the reaction conditions. The average conditions of temperature and pressure existing in a bed may vary depending upon the nature of the catalyst, the nature of the catalyst bed, and upon the catalyst size. Generally, the contact time is from 0.1 to 20 seconds and, preferably, 0.3 to 15 seconds.

EXAMPLES

The following examples all involve the oxydehydrogenation of isobutyric acid to methacrylic acid according to the precedure described above. The reactions were conducted in a tubular fixed bed reactor at 400° C. and the feed rate was 8.5 mls. per hour of isobutyric acid, 30.0 mls. per hour of water, and 120.0 mls per minute of air. The iron/phposphate catalyst used in these examples is composed of iron, cesium, phosphorus, oxygen and silica prepared in the following proportions: $Fe_{1.0}, Cs_{0.1}P_{1.26}O_x/SiO_2$. In the following examples, this is referred to as the standard catalyst. In each of the examples below, the reaction was started with fresh catalyst.

In the following, the percentage conversion indicates the percent of IBA which has reacted and percent selectivity represents the percent of the reacted IBA which has been converted into methacrylic acid. Although it is desirable to obtain the highest values for both conversion and selectivity, selectivity is believed to be the most important indicator of a successful catalyst. If the selectivity is high, there is less wasted IBA; and if the conversion is low, the unused IBA can be recycled into the reactor.

EXAMPLE I

The reactor was packed with the standard catalyst as stated above and run under standard conditions. The following results were obtained:

| Time | Conversion | Selectivity/MAA |
| --- | --- | --- |
| 2 hours | 95% | 76% |
| 20 hours | 90% | 71% |
| 30 hours | 80% | 65% |

This was repeated and the following results were obtained, with fresh catalyst.

| Time | Conversion | Selectivity/MAA |
| --- | --- | --- |
| 24 hours | 97% | 70% |

-continued

| Time | Conversion | Selectivity/MAA |
|---|---|---|
| 48 hours | 80% | 68% |

EXAMPLE II

The standard catalyst was packed in the reactor and phosphoric acid was added to the feed at a rate of 550 ppm. The following results were obtained:

| Time | Conversion | Selectivity |
|---|---|---|
| 2 hours | 95% | 76% |
| 20 hours | 90% | 72% |
| 30 hours | 80% | 70% |

The method of this example is taught by the prior art. As will be apparent from comparison with Example IV, the present invention is a substantial improvement over prior art.

EXAMPLE III

A phosphate-doped support was prepared by mixing 40.0 mls. of concentrated $H_3PO_4$ with 200.0 mls. Ludox 40 H S, (a brand of silica sold by DuPont Company). This mixture was dried at 120° for 12 hours and calcined at 450° C. for 16 hours. This calcined mass was placed in a standard fixed bed tubular reactor and the reactor was operated under the standard conditions stated above without the presence of any of the iron/phosphate catalyst. This support alone converted 2.5 percent of the IBA. The selectivity to methacrylic was only a trace and the selectivity to carbon dioxide was 65%. This indicates that the phosphate-doped silica does not act as a catalyst.

EXAMPLE IV

The following example was conducted using standard feed conditions and temperature in the same reactor as the above examples, the difference being the catalyst was a combination of standard catalyst and the phosphate-doped silica as prepared in Example III, mixed together in dry state at a ratio of 1 to 3 standard catalyst to support. The results of this reaction are listed below:

| Time | Conversion | Selectivity/MAA |
|---|---|---|
| 5 hours | 89% | 84% |
| 43 hours | 88% | 81% |
| 112 hours | 89% | 80% |
| 116 hours | 85% | 80% |

The experiment was stopped after 116 hours without any indication of a decrease in the conversion or selectivity of the catalyst.

This was repeated with fresh catalyst and the following results were obtained:

| Time | Conversion | Selectivity |
|---|---|---|
| 24 hours | 95.0% | 77.0 |
| 48 hours | 95.0% | 81.1 |

The following example is presented to demonstrate that merely adding silica to the catalyst together with additional phosphoric acid when the catalyst is being prepared does not provide a solution to the phosphate leaching problem.

EXAMPLE V

In this example, a hybrid catalyst was prepared. An aqueous slurry of phosphoric acid and silica was combined with an aqueous slurry of an iron salt, phorphoric acid, and a cesium salt. The proportions of iron, phosphorus, cesium and oxygen in this latter slurry were approximately the same as the proportions of elements in the standard catalyst. The combined slurries were dried at 100° C. and calcined at 450° C. for 16 hours.

This calcined catalyst was placed in fixed bed tubular reactor and used to catalyze the oxydehydrogenation of IBA under standard conditions. In this reaction, the conversion of IBA was 69.5% and the selectivity of methacrylic acid was 60%.

Example IV in which the iron phosphate catalyst and the phosphorus-doped silica were prepared separately and the two were mixed together in a dry state, was the most successful catalyst system. Contrary to what the prior art teaches, merely adding phosphorus alone in the form of phosphoric acid in the feed does not solve the problem of phosphate being leached from the catalyst.

As demonstrated by Example IV, physically mixing a phosphate-doped support with the phosphate catalyst in a dry state provides a method to overcome this problem which is superior to other methods disclosed in the prior art.

Having thus described my invention, I claim:

1. A two component catalyst system comprising in physical mixture a phosphate-containing catalyst and a phosphate-doped inert support wherein said support is prepared by forming a liquid solvent slurry of an inert support and a phosphate-containing component, evaporating off the solvent to form a dried mass and calcining this dried mass.

2. The catalyst system as claimed in claim 1 wherein said inert support is selected from the group consisting essentially of silica, titania or zirconia.

3. A catalyst system as claimed in claim 1 wherein said liquid solvent is water and said phosphorus-containing compound is phosphoric acid.

4. A catalyst system as claimed in claim 1 wherein said phosphate-containing catalyst is an iron/phosphate catalyst.

5. A catalyst system as claimed in claim 4 wherein said inert support is silica.

6. A catalyst system as claimed in claim 4 wherein said phosphate-containing component is phosphoric acid and said liquid solvent is water.

7. A two component catalyst system comprising
  (a) a catalyst having the general formula $Fe\ P_xMe_yO_z$ wherein Me represents one or more of the following elements: Li, Na, K, Rb, Cs, Mg, Ca, Sr and Ba;
  x is 0.2 to 2.0;
  y is 0.10 to 2.0; and
  z is an amount of oxygen bound to the other elements and corresponding to their state of oxidation; and
  (b) a support comprising silica and a phosphorus-containing compound wherein said silica and phosphorus-containing compound are combined in a liquid slurry the liquid is evaporated off and the remaining solid is calcined;
and wherein the catalyst and the support are mixed together in a substantially dry state.

* * * * *